(12) United States Patent
Gotman et al.

(10) Patent No.: US 8,300,765 B2
(45) Date of Patent: Oct. 30, 2012

(54) INTERVENTIONAL IMAGING AND DATA PROCESSING

(75) Inventors: Schlomo Gotman, Haifa (IL); Udo Van Stevendaal, Ahrensburg (DE); Peter Forthmann, Sandesneben (DE); Holger Schmitt, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 13/054,103

(22) PCT Filed: Jul. 14, 2009

(86) PCT No.: PCT/IB2009/053049
§ 371 (c)(1),
(2), (4) Date: Jan. 14, 2011

(87) PCT Pub. No.: WO2010/015952
PCT Pub. Date: Feb. 11, 2010

(65) Prior Publication Data
US 2011/0116598 A1    May 19, 2011

Related U.S. Application Data

(60) Provisional application No. 61/085,930, filed on Aug. 4, 2008.

(51) Int. Cl.
*G01N 23/04* (2006.01)
*A61B 6/00* (2006.01)
(52) U.S. Cl. .................. 378/62; 378/4; 382/131
(58) Field of Classification Search ............. 378/4, 62
See application file for complete search history.

(56) References Cited

U.S. PATENT DOCUMENTS

| | | | | |
|---|---|---|---|---|
| 3,765,403 A | * | 10/1973 | Brenden | 600/448 |
| 5,014,709 A | * | 5/1991 | Bjelkhagen et al. | 600/431 |
| 5,185,778 A | | 2/1993 | Magram | |
| 5,474,072 A | * | 12/1995 | Shmulewitz | 600/446 |
| 5,612,985 A | | 3/1997 | Toki et al. | |

(Continued)

FOREIGN PATENT DOCUMENTS

WO    9824064 A1    6/1998

(Continued)

OTHER PUBLICATIONS

Baldazzi, G., et al.; Development of a K-edge micro CT for the Study of Tumor Angiogenesis in Small Animals; 2006; Proc. SPIE; 6142; 61421; abstract.

(Continued)

*Primary Examiner* — Alexander H Taningco (57) ABSTRACT

An imaging system includes a radiation source (110) that emits radiation that traverses an examination region. A controller (116) activates the radiation source (110) to emit radiation and deactivates the radiation source (110) to stop radiation emission. The controller (116) selectively activates the radiation source (110) to emit radiation at one or more predetermined angles. In another embodiment, the imaging system includes a data processing component (124) that generates a virtual three dimensional image of an object of interest of the scanned subject based on the image data. In another embodiment, the imaging system is in a communication with a data manipulation and packaging component (128) that generates at least a two dimensional or a three dimensional data set based on the volumetric image data and packages the data set in an object provided to a remote system (132) that manipulates and navigates through the data set.

8 Claims, 6 Drawing Sheets

U.S. PATENT DOCUMENTS

| | | | |
|---|---|---|---|
| 6,697,067 B1 | 2/2004 | Callahan et al. | |
| 6,771,402 B2 * | 8/2004 | Snider | 359/9 |
| 6,947,584 B1 | 9/2005 | Avila et al. | |
| 7,277,523 B2 | 10/2007 | Mattson | |
| 7,340,032 B2 | 3/2008 | Besson | |
| 2004/0153128 A1 * | 8/2004 | Suresh et al. | 607/14 |
| 2005/0057787 A1 * | 3/2005 | Nakamura | 359/3 |
| 2005/0122549 A1 * | 6/2005 | Goulanian et al. | 359/3 |
| 2006/0215817 A1 | 9/2006 | Watanabe | |
| 2007/0189438 A1 | 8/2007 | Popescu | |
| 2007/0269011 A1 | 11/2007 | Sandkamp et al. | |
| 2007/0287901 A1 * | 12/2007 | Strommer et al. | 600/407 |
| 2009/0237759 A1 * | 9/2009 | Maschke | 359/9 |
| 2010/0020926 A1 * | 1/2010 | Boese et al. | 378/44 |

FOREIGN PATENT DOCUMENTS

WO     2006085266 A1     8/2006

OTHER PUBLICATIONS

Grasruck, M., et al.; Combination of CT Scanning and Fluroscopy Imaging on a Flat-Panel CT Scanner; 2006; Proc. SPIE; 6142; 61422J; abstract.

Robb, R. A.; 3-D Visualization and Analysis in Prostate Cancer; 2002; Drugs Today; 38(3)153-169.

ScienceDaily; Life-Sized Holograms; 2006; http://www.sciencedaily.com/videos/2006/0510-lifesized_holograms.htm.

* cited by examiner

INTERVENTIONAL IMAGING AND DATA PROCESSING

CROSS REFERENCE TO RELATED APPLICATIONS

This application claims the benefit of U.S. provisional application Ser. No. 61/085,930 filed Aug. 4, 2008, which is incorporated herein by reference.

The following generally relates to interventional imaging and data processing, and finds particular application to computed tomography (CT). However, it also amenable to other medical imaging applications and to non-medical imaging applications.

Radiographic imaging is routinely used during interventional procedures such as biopsies, ablation, and drainage to facilitate navigating instruments with respect to anatomical structures. A C-Arm imaging system is often used with such procedures to acquire data for real-time radiographic imaging. With a C-arm, the operator manually rotates the arm to capture data from an angle of interest. CT Fluoroscopy has also been used with such procedures. CT images, generally, provide better anatomical information relative to x-ray images, and, in some instances, are used to generate radiographic images. Unfortunately, generating such images may include an intensive and time-consuming process, which is not well-suited for real-time procedures like interventional procedures, and the resulting images are two-dimensional, and lack a 3D impression, even when the object of interest is volumetric by nature (i.e., anatomical structures). Furthermore, CT procedures typically include higher radiation dose with less z-axis coverage relative to C-arm procedures. Moreover, CT images are generated in axial orientation. To obtain alternative views such as coronal or a sagittal view, multiple slices have to be acquired and reformatted, which requires significant computing power.

Diagnostic imaging often involves usage of 3D imaging, including navigation through 3D data sets. To create and navigate through such data sets, the end-user needs access to appropriate tools and access to the original data. A common practice is to send the original CT data to a dedicated high end processing workstation, either directly or after archiving the data on a PACS (Picture Archiving and Communication System) or other system. A user with access to the processing workstation invokes a suitable application, and creates and navigates through the 3D data sets. However, generating the 3D data sets can be time-consuming, requiring the loading of large data sets and execution of sophisticated applications for segmentation, registration/fusion, correction of automatically-generated results, etc. In addition, 3D data sets may not be available to an end user, such as a physician, outside of the hospital and/or such an end user may not have a workstation capable of loading, creating, manipulating and navigating through 3D data. In some instance, static 3D images are prepared from the 3D data and made available for viewing outside of the hospital. Unfortunately, such images cannot be manipulated or navigated through.

Aspects of the present application address the above-referenced matters and others.

In one aspect, an imaging system includes a radiation source that emits radiation that traverses an examination region. A controller activates the radiation source to emit radiation and deactivates the radiation source to stop radiation emission. The controller selectively activates the radiation source to emit radiation at one or more pre-determined angles. A detector array, located across from the radiation source opposite the examination region, detects radiation that traverses the examination region and generates a signal indicative thereof. A reconstructor reconstructs the signal to generate image data used to create one or more radiographic images corresponding to the one or more pre-determined angles.

In another aspect, an imaging system includes a radiation source that emits radiation that traverses an examination region and a detector array, located across from the radiation source opposite the examination region, that detects radiation that traverses the examination region and generates a signal indicative of the examination region and a subject disposed therein. A reconstructor reconstructs the signal to generate image data indicative of the signal. A data processing component generates a virtual three dimensional image of an object of interest of the scanned subject based on the image data.

In another aspect, an imaging system includes a radiation source that emits radiation that traverses an examination region. A detector array, located across from the radiation source opposite the examination region, detects radiation that traverses the examination region and generates a signal indicative thereof. A reconstructor reconstructs the signal to generate volumetric image data indicative of the signal. A data manipulation and packaging component generates at least a two dimensional or a three dimensional data set based on the volumetric image data and packages the data set in an object provided to a remote system that manipulates and navigates through the data set.

In another aspect, a method includes employing a computed tomography imaging system to selectively acquire data at an angle of interest, reconstructing the acquired data, and generating a radiographic image corresponding to the angle of interest.

In another aspect, a method includes performing a scan of a region of interest of a subject, reconstructing data acquired during the scan to generate volumetric image data indicative of the region of interest, and processing the volumetric image data to generate a virtual three dimensional image of the region of interest.

In another aspect, a method includes reconstructing data acquired by an imaging system, producing at least a two dimensional or a three dimensional data set based on the reconstructed data, packaging the data set in an object, and providing the object to a remote system.

The invention may take form in various components and arrangements of components, and in various steps and arrangements of steps. The drawings are only for purposes of illustrating the preferred embodiments and are not to be construed as limiting the invention.

Figure 1:
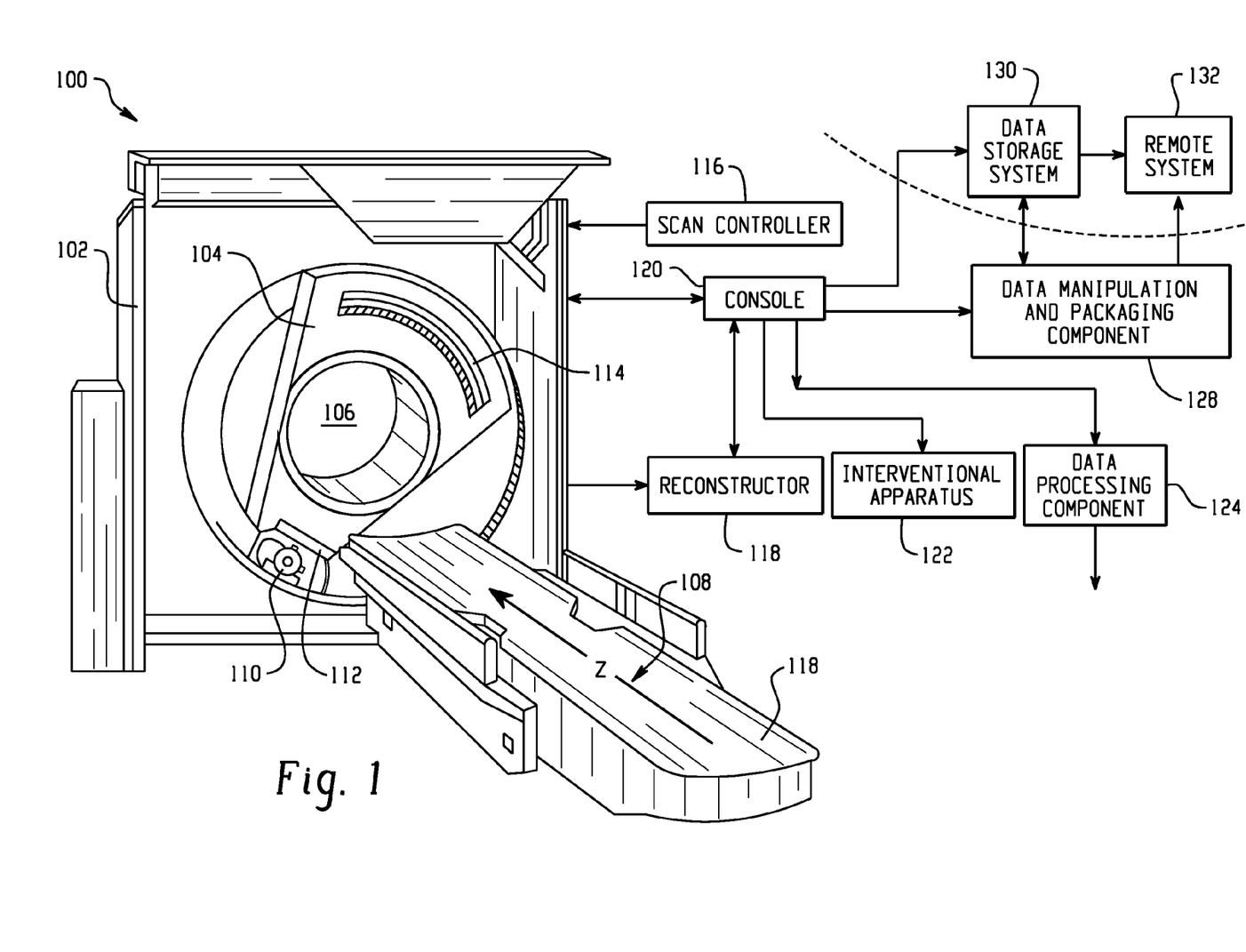
FIG. 1 illustrates an example imaging system.

FIG. 1 illustrates a computed tomography (CT) scanner 100 that includes a stationary gantry 102 and a rotating gantry 104, which is rotatably supported by the stationary gantry 102. The rotating gantry 104 rotates around an examination region 106 about a longitudinal or z-axis 108. A radiation source 110, such as an x-ray tube, is supported by and rotates with the rotating gantry 104 around the examination region 106. The radiation source 110 emits radiation, which is collimated by a collimator 112 to produce a generally fan, wedge, or cone shaped radiation beam that traverses the examination region 106.

A radiation sensitive detector array 114 detects photons that traverse the examination region 106 and generates projection data indicative thereof. A reconstructor 118 reconstructs the projection data and generates image data indicative of the examination region 106, including a portion of a subject residing therein. A general purpose computing system 120 serves as an operator console. Software resident on the console 120 allows the operator to control the operation of the system 100. This may include allowing the operator to select a protocol employed with an interventional procedure, generating a virtual 3D data, creating one or more images based on the volumetric image data, allowing the operator to transfer the data to another component or system, and/or other operations.

An interventional apparatus 122, used for interventional procedures such as biopsies, ablation, drainage and/or other interventional procedures, is in communication and operates in conjunction with the scanner 100. As such, the scanner 100 may be used to generate image data and/or one or more images that facilitate performing an interventional procedure in connection with the interventional apparatus 122. This may include generating one or more radiographic images and/or virtual 3D data reconstructions for a procedure.

In one embodiment, a human actuated scan controller 116 is used to start and stop scanning, or turn x-rays on and off. In one instance, the human actuated scan controller 116 includes at least one foot pedal with at least two positions, one for starting scanning and one for stopping scanning In other embodiments, other devices such as a joystick or the like allow the user to starts and stops scanning In the illustrated embodiment, the human actuated scan controller 116 is located in the scanner room, thereby allowing the user to start and stop scanning during a procedure such as an interventional or surgical procedure. In another embodiment, the scan controller 116 is located otherwise, for example, outside of the scanner room. In such an instance, another user outside of the scanner room employs the scan controller 116 to start and stop scanning In other embodiments, the human actuated scan controller 116 is omitted.

Additionally or alternatively, a data processing component 124 generates one or more images that facilitate performing an interventional procedure with the interventional apparatus 122. As described in greater detail below, the data processing component 124 can generate a virtual 3D dimensional reconstruction such as a hologram of a region of interest, and such a reconstruction can be displayed during an interventional procedure to facilitate performing the interventional procedure. In other embodiments, data processing component 124 is omitted.

Additionally or alternatively, a data manipulation and packaging component 128 generates 2D and 3D object data sets and packages the data sets based on the imaging procedure or otherwise. As described in greater detail below, this includes generating 2D and 3D renderings and packing the renderings in DICOM and non-DICOM formats. The packaged data can be stored on portable medium such as CD, DVD, memory stick, etc. and transported and provided to various systems and/or other medium such as a hard drive, a database, a server, a web service, archiving system such a PACS (Picture Archiving and Communication System). A remote system 132 is used to view the packaged data. Depending on the packaged data and the application tools available to the remote system 132, the viewing may include tools such as rotate, pan, zoom, segment, loop, etc. The remote system 132 can obtain the packaged data via the portable medium and/or over a link via query or other data retrieval instruction. In other embodiments, the data manipulation and packaging component 128 and the remote system 132 are omitted.

Figure 2:
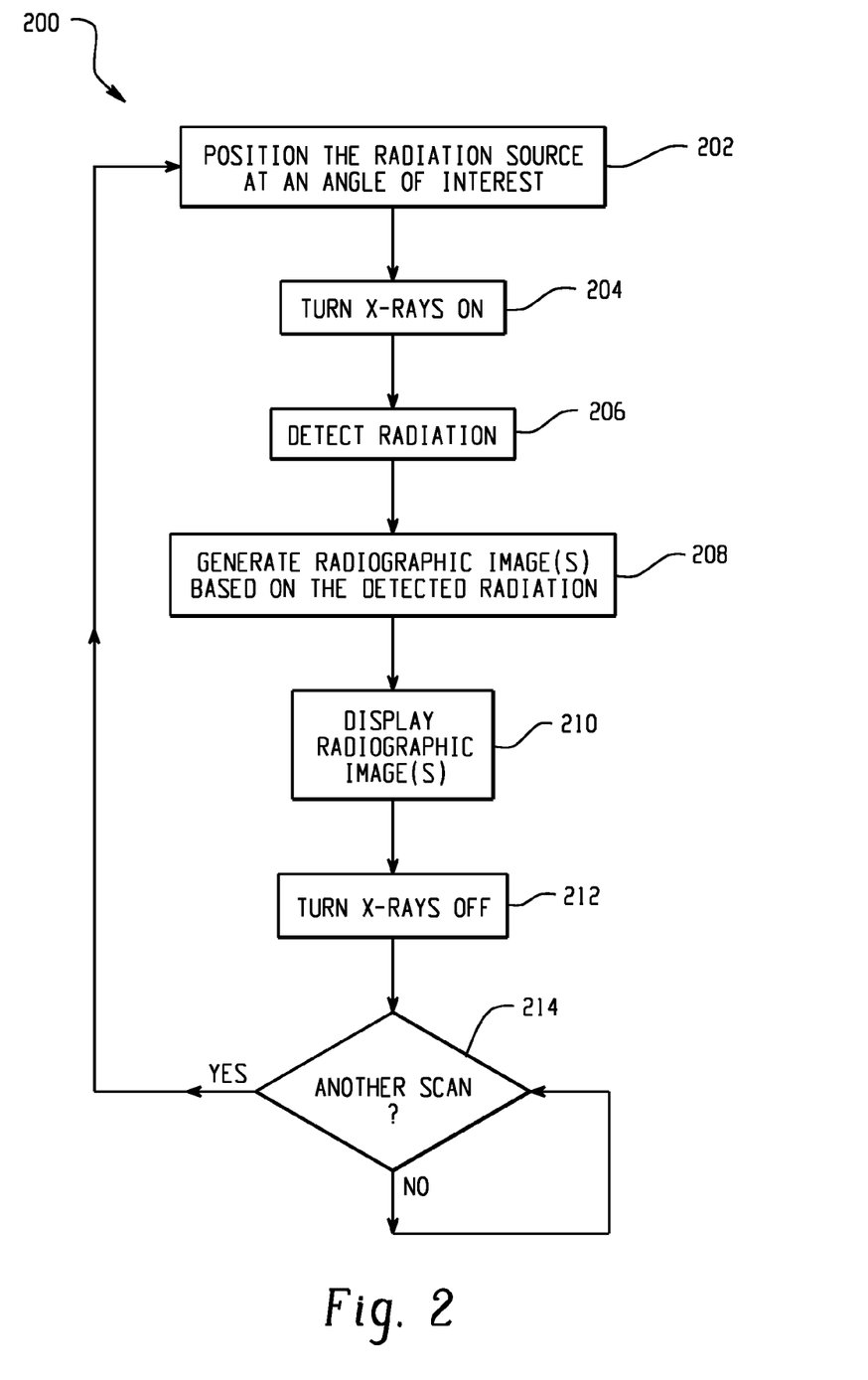
FIGS. 2, 3, and 4 illustrate example techniques for generating radiographic images using a CT scanner.
Figure 3:
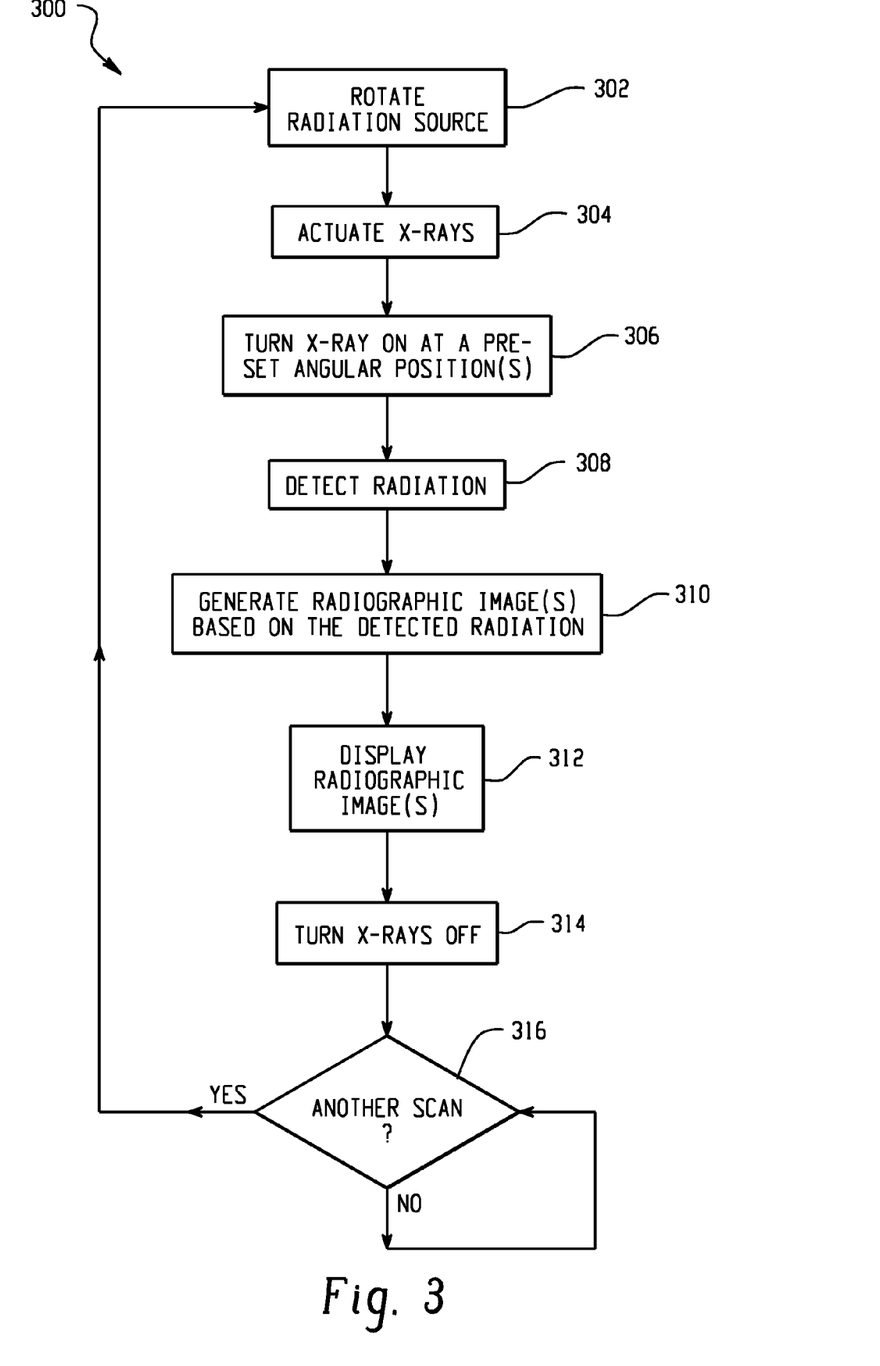
Figure 4:
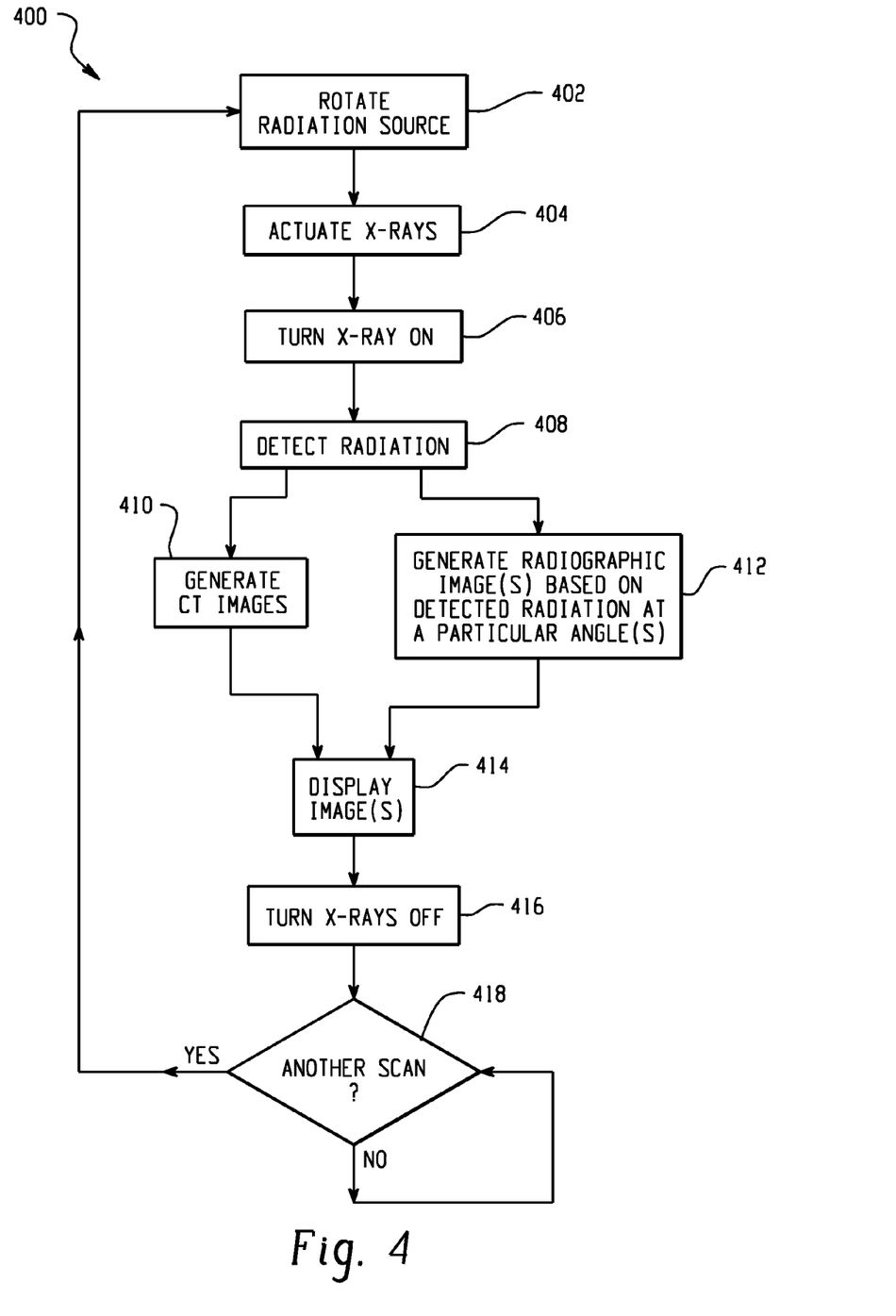

As noted above, the human actuated scan controller 116 can be used to start and stop scanning in conjunction with a procedure such as an interventional procedure. FIGS. 2, 3, and 4 illustrate various techniques for employing the scan controller 116 and scanner 100 to at least selectively acquire data and generate radiographic images that can be used to facilitate performing such a procedure.

Initially referring to FIG. 2, a method 200 for generating radiographic images with the radiation source 110 parked at a particular angular position is illustrated. At 202, the rotating gantry 104 is rotated to position and park the radiation source 110 supported thereby at a particular angle, which may be defined by the operator or the selected protocol via the console 120, for scanning, unless the radiation source 110 is already parked at the desired angle. At 204, the human actuated scan controller 116 is actuated to turn x-rays on, which results in emission of radiation, by the radiation source 110, that traverses the examination region 106. Where the scan controller 116 is a foot pedal, this may include pressing on and urging the foot pedal down until a position is reached where an activate x-rays signal is generated. Where the scan controller 116 is a joy stick, this may include moving the joy stick to a position where an activate x-rays signal is generated.

At 206, the radiation detector array 114 detects radiation traversing the examination region. As noted above, the detector array 114 generates a signal indicative thereof, and the reconstructor 118 reconstructs the signal to generate image data. At 208, the console 120 generates one or more radiographic images from the image data. At 210, the one or more images are displayed. In one instance, generated images are consecutively displayed in a same display region. Additionally or alternatively, multiple images are concurrently displayed in different display regions. Additionally or alternatively, the user may select a particular image(s) to display. At 212, the scan controller 116 is used to turn x-rays off. With the foot pedal, this may include depressing or letting the foot pedal return to a position where x-rays are not turned on, or further pressing the foot pedal to a turn off x-rays position. With the joy stick, this may include moving or releasing the joy stick and letting the joy stick return to a position where x-rays are not turned on.

At 214, it is determined whether another scan is to be performed. For example, actuating the scan controller 116 again turns x-rays on again, and acts 202 to 214 can be repeated. Otherwise, x-rays remain off. It is to be appreciated that acts 202 to 214 can be performed one or more times at the same or at one or more different angles. For example, the scan angle can be changed between scans, with acts 202-214 subsequently being repeated. In one instance, the foregoing provides for real-time acquisition of low-dose radiography images on a CT scanner at an angle of interest by generating images with data acquired with a stationary (or non rotating) radiation source 110. Such images may be used to facilitate interventional procedures such as, for example, navigating an interventional instrument through the anatomy.

FIG. 3 illustrates a method 300 for generating radiographic images with data obtained at a particular angle while the radiation source 110 rotates about the examination region 106. At 302, the rotating gantry 104 ramps up to a pre-set scanning speed, for example, as determined by a selected scan protocol, if not already rotating at the pre-set scanning speed. At 304, the human actuated scan controller 116 is actuated. At 306, the radiation source is controlled to automatically emit radiation at at least one pre-set angular position as the radiation source 110 rotates around the examination region 106, including, but not limited to, every time the radiation source 110 rotates around the examination region 106.

At 308, the radiation detector array 114 detects radiation traversing the examination region 106. At 310, one or more radiographic images are generated based on the detected radiation. At 312, the one or more images are displayed. At 314, the scan controller 116 is employed to turn x-rays off. The radiation source 110 may or may not continue to rotate. At 316, it is determined whether another scan is to be performed. For example, actuating the scan controller 116 again turns x-rays on again, and acts 302 to 316 can be repeated. Otherwise, x-rays remain off. Likewise, the acts 302 to 316 can be performed one or more times at the same or at one or more different angles. The operator may change the scan angle between scans or during scanning When doing so during scanning, the change may take effect at latest during the next rotation or otherwise.

In one instance, the foregoing provides for fast (near real-time) acquisition of low-dose radiography images by the scanner 100 by selectively turning the x-ray on/off and generating an image(s) during gantry rotation at one or more angle ranges. Generally, the frame rate of the displayed images may be defined by the gantry rotation speed, for example, 5 frames/sec for a 0.2 sec rotation time or otherwise. Of course, other frame rates, including higher and lower frame rates, are contemplated herein. The resulting images may be used to facilitate procedures such as, for example, navigating an interventional instrument through the anatomy.

FIG. 4 illustrates a method 400 for concurrently generating radiographic and CT images. At 402, the rotating gantry 104 ramps up to a pre-set scanning speed, for example, as determined by a selected scan protocol, if not already rotating at the pre-set scanning speed. At 404, the human actuated scan controller 116 is actuated. Alternatively, scanning can be activated at the console 120. At 406, the radiation source 110 continuously emits radiation. At 408, the radiation detector array 114 detects radiation traversing the examination region 106. At 410, one or more radiographic images are generated based on the detected radiation detected at one or more angular position, and at 412 one or more CT images are generated based on the detected radiation. It is to be appreciated that the radiographic and CT images can be serially or concurrently generated.

At 414, the images are displayed. At 416, x-rays are turned off. Similar to above, the radiation source 110 may or may not continue to rotate. At 418, it is determined whether another scan is to be performed. For example, x-rays can be turned on again, with acts 402 to 418 being repeated. Otherwise, x-rays remain off. Likewise, the acts 402 to 418 can be performed one or more times with a radiographic image being generated with data corresponding to a particular angle. Generally, this approach provides for relatively faster (shorter than 0.2 seconds) generation of radiographic images than the method 300. In addition, radiographic images can be generated for any angle since data is continuously captured as the radiation source 110 rotates and emits radiation.

Figure 5:
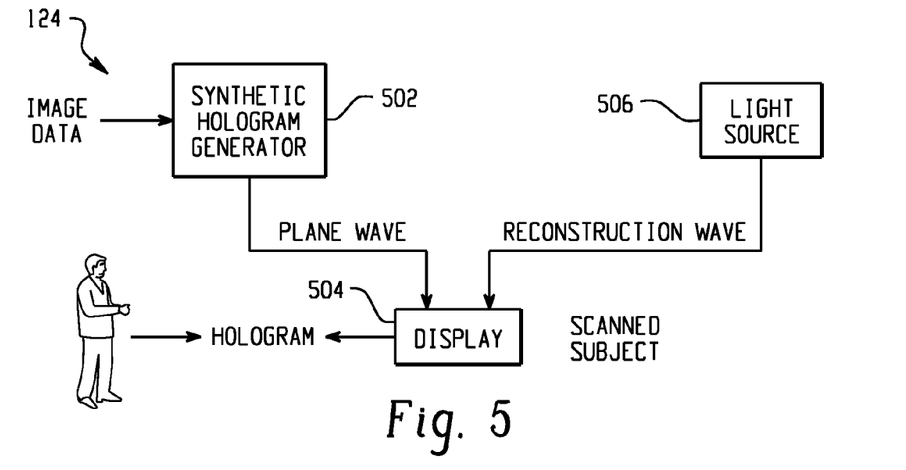
FIGS. 5 and 6 illustrate an example in which a hologram is generated from CT image data.

The above methods can be used with interventional procedures. As noted previously, the resulting images generally are 2D or 3D dimensional renderings displayed on a 2D monitor. FIG. 5 illustrates a data processing component 124 that generates a virtual 3D dimensional volume such as a 3D hologram and a display 504 that generates the hologram. The hologram can be used to facilitate performing interventional as well as other procedures.

The data processing component 124 can generate various types of holograms including, but not limited to, a transmission hologram, a rainbow hologram, a reflection hologram and/or other holograms. Generally, transmission holograms are viewed by shining laser light through them and looking at the reconstructed image from the side of the hologram opposite the source, a rainbow transmission hologram allows more convenient illumination by white light rather than by lasers or other monochromatic sources, and reflection hologram is capable of multicolor image reproduction using a white light illumination source on the same side of the hologram as the viewer. For sake of brevity and explanatory purposes, the data processing component 124 is discussed in connection with a transmission hologram.

The data processing component 124 generates a transmission hologram based on the image data, including a segmented portion thereof. In general, a synthetic hologram generator 502 generates a synthetic hologram plane wave, based on the image data, which includes, in one instance, a plurality of relatively very small black (absorption) and white (transmission) pixels. This can be done for all or a subset of the voxels in the image data. The synthetic hologram is provided to a display 504, which, in this instance, is a display that absorbs and reflects light such as an electro-optic display like a liquid crystal display (LCD) or other suitable display. Other display types are also contemplated herein.

A light source 506 such as a laser or other light serves as the reference or reconstruction beam, and illuminates the display 504 to reconstruct the hologram. The reference beam carries the phase information and, at the hologram, diffracts and thereby reconstructs the hologram, which the operator observes as a 3D impression or virtual image located at the position of region of interest in the scanned subject. In one instance, the hologram is displayed using a grey scale and showing depth information, which changes as the user changes the line of sight.

Figure 6:
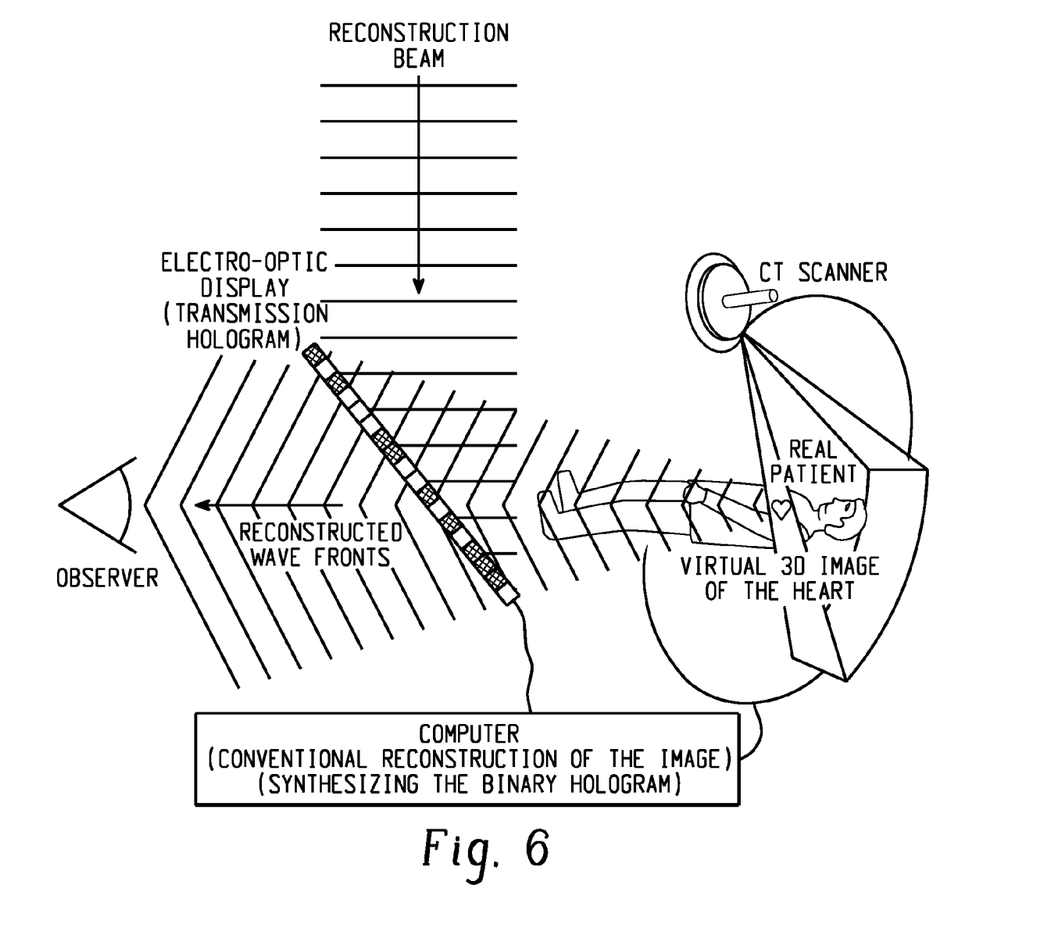

It is to be appreciated that such a hologram may facilitate performing an interventional procedure. Data acquisition during the interventions and real time reconstruction and synthesizing of the binary hologram allows for real time guidance. The hologram may not only provide an impression of a 3D view, but the view is a true virtual three dimensional copy, unlike a 3D volume rendering display on a 2D monitor. The user can use the hologram to track, for example, a stent in 3D while it is implanted. When the user looks through the hologram at the subject, the user will see the 3D copy of the organ at its real position without obstructing the user's sight to the patient. This is shown in FIG. 6 in which the object under investigation is the heart. In other embodiment, other organs may be of interest. Observing the hologram by changing the line of sight allows the user to look around the structure including behind structures to view otherwise obstructed regions.

Figure 7:
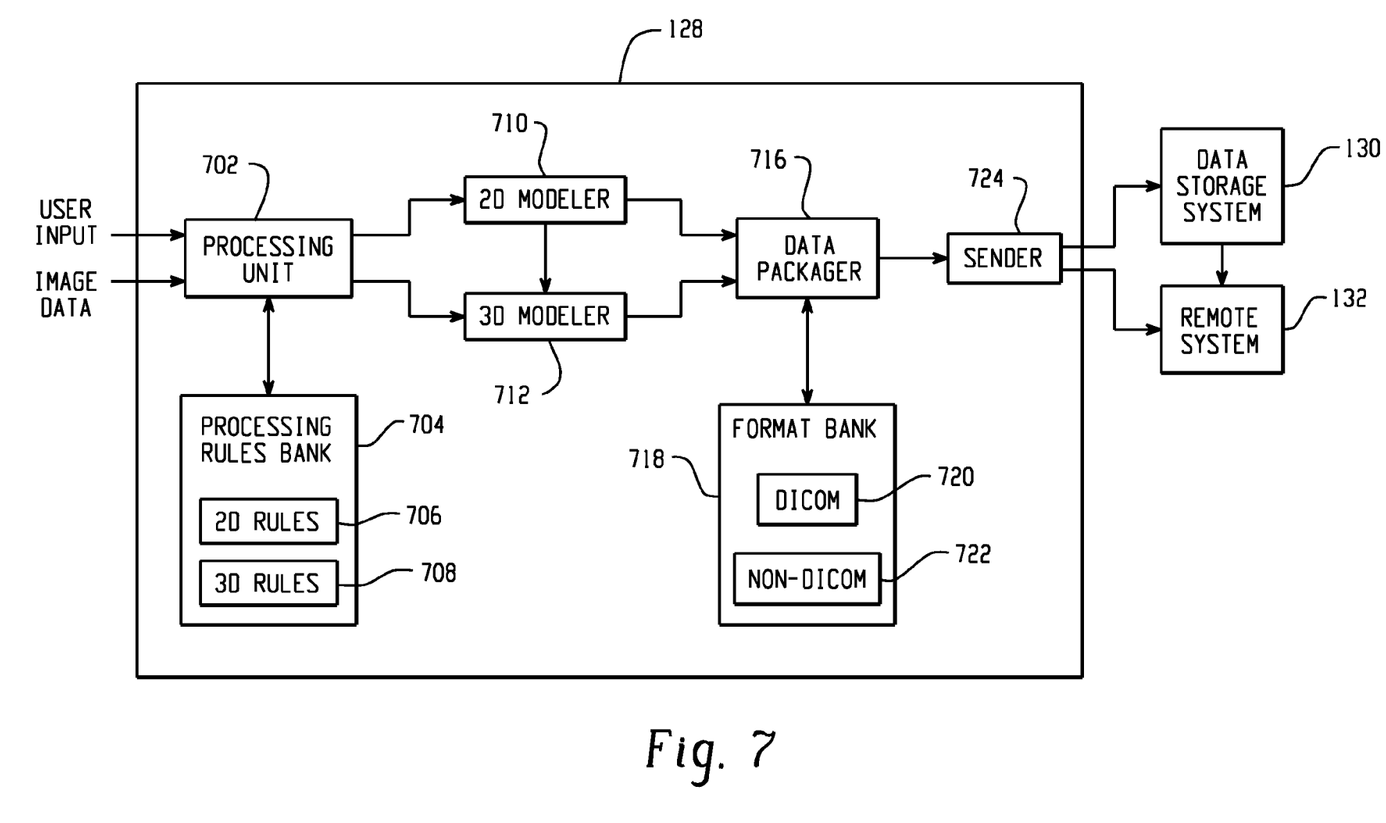
FIG. 7 illustrates an example data manipulation and packaging component.

FIG. 7 illustrates an example of the data manipulation and packaging component 128. Although described in connection to the CT scanner 100, it is to be understood that the data provided to the data manipulation and packaging component 128 can be from other imaging systems such as, but not limited to, positron emission (PET), single photon emission CT (SPECT), ultrasound (US), magnetic resonance imaging (MRI), and/or other imaging system.

In this example, the data manipulation and packaging component 128 includes a processing unit 702 that obtains the 2D image data from the scanner 100. Such data may be conveyed in DICOM (Digital Imaging and Communications in Medicine) or another format. The processing unit 702 determines how the image data is to be processed. In one instance, the image data includes information such as attributes and/or parameters, and the processing unit 702 extracts such information and uses the information to determine how to process the data.

A rules bank 704 includes one or more pre-set rules for processing the image data. It is to be appreciated that the pre-set rules may be determined prior to, during and/or subsequent to the scanning procedure. In addition, such rules may include 2D rules 706 for generating 2D data, including individual images and/or a sequence of images, and/or 3D rules 708 for generating 3D data. In one instance, the extracted data may be used to determine the particular pre-set rule used to process the image data. In another instance, the type of imaging procedure, which may be coded in or sent along with the image data, determines the processing rule to employ to process the data. In yet another instance, a user determines the processing rule.

A 2D data modeler 710 generates 2D data sets (e.g., 2D navigation objects) based on the image data when the pre-set rules or user determines that 2D data is to be generated from the image data. In one instance, the 2D data modeler 710 automatically generates a 2D data set, while in another instance the 2D data modeler 710 generates a 2D data set with user interaction. Depending on the pre-set rule, such data may be one or more individual images, a sequence of images to be scrolled through in a predefined order, etc. Such images can be generated in various formats, including, but not limited to, JPG, TIFF, BMP, GIF, PCX, or another image format. Sequences of images may also be used to generate video files, for example, in an MPEG, AMV, AVS or another video format.

A 3D data modeler 712 generates 3D data sets (e.g., 3D navigation objects) based on the image data and/or a 2D data set when the pre-set rules or user determines that 3D data is to be generated from the image data. The 3D data may include one or more of surface and volume renderings, segmented data, etc., and may be automatically generated or generated with user interaction. For instance, the 3D rules 708 may determine that particular image data corresponding to a head scan should be automatically processed to generate a surface-rendered 3D image of the skull. In another example, the 3D rules 708 may determine that particular image data corresponding to gastro intestinal tract should be processed to generate an endoscopic view along a path defined with or without user interaction. 3D data can be generated in various formats, including, but not limited to, mesh (.x), STL, IGES, PARASOLID, STEP, or another 3D format. The 3D data may also include a stacked series of 2D data, such as 2D data generated by the 2D data modeler 710.

A data packager 716 packages or encapsulates the generated data. A format bank 718 includes one or more packaging formats, including at least a DICOM format 720. A DICOM format allows encapsulation of the data with the patient and examination information. As shown, the format bank 718 may also include one or more non-DICOM formats 722. In one embodiment, private attributes are used when employing a non-DICOM format. As such, the data packager 716 may include a signature with a generated data package.

A sender 724 provides the packaged data to the data storage system(s) 130 and/or the remote system(s) 132. The remote system 132 includes a suitable application for extracting the generated data from the packaged data. Such an application may be a conventional viewing application, such as a plug-in or a dedicated program, which provides viewing, manipulation, and/or navigation tools. By way of example, when the generated data is a sequence of JPG images, a conventional JPG viewer can be used to scroll through the sequence. In another example, when the generated data is a volume mesh, a conventional mesh viewer such as an open-source mesh viewer may be used for viewing and navigation.

The above may be implemented by way of computer readable instructions, which, when executed by a computer processor(s), causes the processor(s) to carry out the acts described herein. In such a case, the instructions are stored in a computer readable storage medium such as memory associated with and/or otherwise accessible to the relevant computer.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. An imaging system, comprising:
   a radiation source that emits radiation that traverses an examination region;
   a detector array, located across from the radiation source opposite the examination region, that detects radiation that traverses the examination region and generates a signal indicative of the examination region and a subject disposed therein;
   a reconstructor that reconstructs the signal to generate image data indicative of the signal;
   a data processing component that generates a virtual three dimensional image of an object of interest of the scanned subject based on the image data;
   a synthetic hologram generator that generates a synthetic hologram including absorption and transmission pixels based on the image data;
   a display that displays the synthetic hologram; and
   a light source that illuminates the synthetic hologram to reconstruct the virtual three dimensional image of the object of interest.

2. The imaging system of claim 1, wherein the virtual three dimensional image is a hologram.

3. The imaging system of claim 1, wherein the display is positioned between a user and the examination region so that the virtual three dimensional image appears to be positioned substantially at the location of anatomy represented by the virtual three dimensional image.

4. The imaging system of claim 1, wherein the virtual three dimensional image is generated in real time as the image data is reconstructed.

5. The imaging system of claim 1, wherein the virtual three dimensional image is used to guide an instrument during an interventional procedure.

6. A method, comprising:
   performing a scan of a region of interest of a subject;
   reconstructing data acquired during the scan to generate volumetric image data indicative of the region of interest;
   processing the volumetric image data to generate a virtual three dimensional image of the region of interest;
   generating a synthetic hologram including absorption and transmission pixels based on the image data;
   displaying the synthetic hologram; and
   illuminating the synthetic hologram to reconstruct the virtual three dimensional image of the object of interest.

7. The method of claim 6, wherein the virtual three dimensional image is a hologram.

8. The method of claim 6, further including projecting the virtual three dimensional image between a clinician and the subject, wherein the virtual three dimensional image is presented at a location of the region of interest.

* * * * *